United States Patent [19]

Hrushesky

[11] Patent Number: 4,675,006
[45] Date of Patent: Jun. 23, 1987

[54] NEEDLE SUPPORT SYSTEM

[75] Inventor: William J. M. Hrushesky, Minneapolis, Minn.

[73] Assignee: Regents of the University of Minnesota, Minneapolis, Minn.

[21] Appl. No.: 816,384

[22] Filed: Jan. 6, 1986

[51] Int. Cl.⁴ ............................................. A61M 5/32
[52] U.S. Cl. .................................. 604/180; 604/174; 128/DIG. 26
[58] Field of Search .............................. 604/174–180; 128/DIG. 26, 640

[56] References Cited

U.S. PATENT DOCUMENTS

| | | | |
|---|---|---|---|
| 2,280,915 | 4/1942 | Johnson | 604/179 |
| 3,487,837 | 1/1970 | Petersen | 604/180 |
| 3,683,911 | 8/1972 | McCormick | 604/180 |
| 3,900,026 | 8/1975 | Wagner | 604/174 |
| 3,957,048 | 5/1976 | Jacobs | 604/180 |
| 4,040,427 | 8/1977 | Winnie | 604/180 |
| 4,235,234 | 11/1980 | Whitney et al. | 604/177 |
| 4,464,178 | 8/1984 | Dalton | 604/174 |
| 4,516,968 | 5/1985 | Marshall et al. | 604/174 |
| 4,519,793 | 5/1985 | Galindo | 604/180 |
| 4,579,120 | 4/1986 | MacGregor | 604/180 |
| 4,645,492 | 2/1987 | Weeks | 604/174 |

OTHER PUBLICATIONS

Brochure of Gish Biomedical, Inc. dated Dec., 1985, Photograph A Showing Vastack Needle Support System.
Photograph B Showing Information Sheet of a Package for a Vascular Implant Access Needle A-AVIA-0-4-019.
Photographs C & D Showing the Vascular Implant Needle of A-AVIA-04-019.
Gish Biomedical, Inc price list dated Aug. 1, 1986.

Primary Examiner—John D. Yasko
Assistant Examiner—Gene B. Kartchner
Attorney, Agent, or Firm—Merchant, Gould, Smith Edell, Welter & Schmidt

[57] ABSTRACT

A needle support is disclosed for supporting a needle inserted into a body part of a patient. The needle support is a frusto-conical member formed from a pair of semiconical halves which are joined at a common hinge edge with the halves presenting opposing flat surfaces which may be pivoted to a closed position with the surfaces opposing and abutting one another. The needle support 50 is formed of a material which is sufficiently rigid to support a needle disposed between said conical halves yet deformable about a rigid needle with deformable portions defining a needle receiving channel. A support base is provided secured to the body portion and sized to cover a part of a patient's skin and adhesive is provided on a skin abutting surface of the support base.

6 Claims, 2 Drawing Figures

NEEDLE SUPPORT SYSTEM

BACKGROUND OF THE INVENTION

I. Field of the Invention

This invention pertains to systems for providing therapeutic fluids to selected sites in a patient's body. More particularly, this invention relates to a device for supporting a needle transferring fluids to a subcutaneous drug administering device.

II. Description of the Prior Art

The art of drug administration is known to include fluid receptacles which are implanted beneath the skin of a patient. From time to time, these receptacles are filled by hypodermic injection with a multidose quantity of a drug which is delivered to a site in the patient's body. The drug is delivered from the receptacle by a catheter which is also surgically implanted beneath the skin. Alternatively, the drug can be administered via a drug-permeable membrane. Such devices include implantable pumps which are located by palpitation and are mechanically pumped to administer the drug. Also included are diaphragms with catheters implanted beneath the skin.

Implantable fluid reservoirs have several advantages in treating a patient. One advantage is the reservoir can be used without the need for a catheter extending through an incision in the patient's skin for administering a fluid to a desired site. The fluid reservoir is filled from time to time by use of a transcutaneous conduit such as a hollow needle which is inserted through the skin into the reservoir. Such reservoirs are provided with walls which are puncturable by needles but reseal upon withdrawal of the needle. A needle currently approved for use with such receptacles is the well-known Huber needle which, due to the configuration of the needle tip, minimizes damage to the self-sealing membrane of the reservoir.

A current problem associated with transcutaneous transfers of fluid through a needle into a subcutaneous drug reservoir is the prior art has not found an adequate way to support the needle during injection. Such injections may last a matter of minutes or a matter of hours. In any event, the needle must remain secured to the patient to ensure the needle is not accidentally removed from the drug reservoir. Historically, a person administering the drug must tape the needle to the patient's body by improvising an anchor formed of adhesive tape. However, such an approach is not always effective and is frequently time consuming and cumbersome. A prior art apparatus which addresses this problem and attempts to provide a solution is U.S. Pat. No. 4,464,178 to Dalton dated Aug. 7, 1984. Dalton teaches an anchor for a transcutaneous fluid delivery conduit such as a hypodermic needle. The anchor comprises a protective boot which includes a plurality of concentric annular rings having inside and outside peripheries. The rings are stacked using the needle as an axis. The stacked rings provide shock absorbing extension and compression along the needle axis. The apparatus of Dalton remains in place between drug administrations. Therefore, the apparatus of Dalton provides means for reducing the number of required injections through a patient's skin. However, the apparatus of Dalton does not appear to be a practical anchor for use of an occasional injection into a reservoir where the presence of an anchor is not desired on a continuous basis. In such cases, the apparatus of Dalton would be a cumbersome apparatus to use to support a needle during transcutaneous injection.

OBJECTS AND SUMMARY OF THE PRESENT INVENTION

It is an object of the present invention to provide an apparatus for anchoring a needle during injection of a drug into a patient.

A further object of the present invention is to provide an apparatus for anchoring a needle during transcutaneous injection into a drug receiving reservoir surgically implanted into a patient.

A still further object of the present invention is to provide an anchor for a needle where the anchor is capable of being quickly and readily secured to both the needle and a patient's body.

A still further object of the present invention is to provide an anchor which is easy to manufacture and relatively inexpensive to permit economic one-time use of the anchor.

According to a preferred embodiment of the present invention, an anchor is provided for securely holding and protecting an injection needle during transcutaneous injection of a drug into a subcutaneous reservoir. The anchor comprises a frusto-conical support member consisting of a first semiconical half and a second semi-conical half which are hinged together along a common edge. The support elements are fabricated from any suitable rigid material which has a surface which will deform around an injection needle. Means are provided for closing the support elements in a closed position with opposing surfaces of the support elements abutting one another with an injection needle disposed between the support elements. A base member is provided secured to the support elements and sized to be received on a patient's body. Any suitable adhesive secures the base member to the patient's skin.

DESCRIPTION OF THE PREFERRED EMBODIMENT

Figure 1:
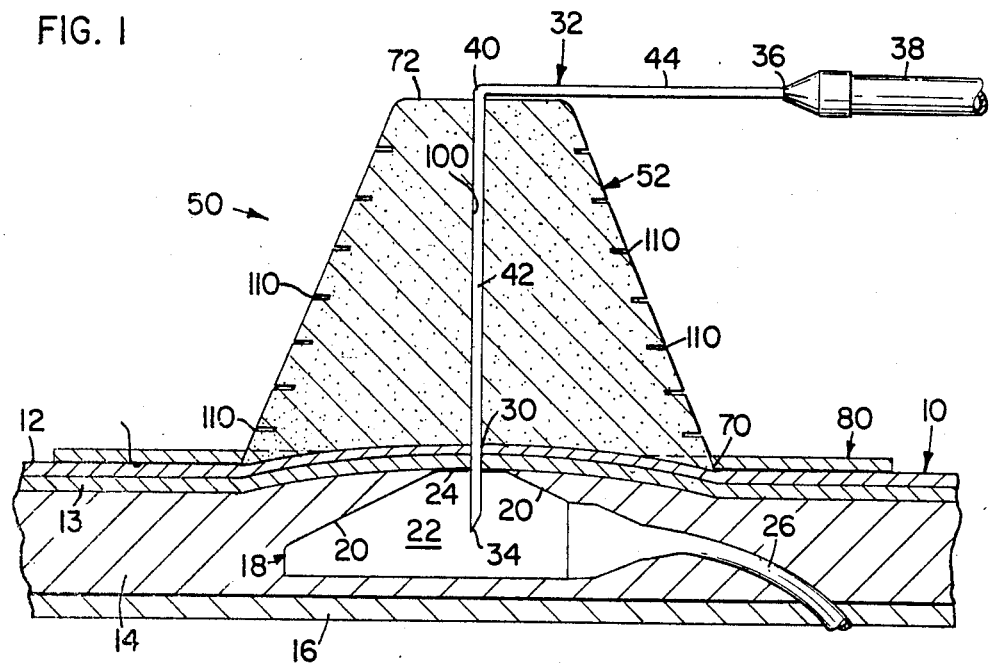
FIG. 1 is a cross sectional view taken in elevation of a needle support of the present invention.

The invention disclosed in the figures of the drawings is designed to inject fluids into a subcutaneous layer of a patient. With reference to FIG. 1, a patient's skin is shown generally at 10 and includes an outer epidermis layer 12 and an inner dermis layer 13. A subcutaneous fat layer 14 is disposed beneath the dermis 13 and a layer of muscle tissue 16.

A fluid receptacle 18 is shown surgically implanted within the subcutaneous layer 14. The fluid receptacle 18 may be any one of a number of implantable receptacles such as implantable pumps or a catheter access port. For purposes of this description, the fluid receptacle 18 is shown as a catheter access port which is surgically implanted within the subcutaneous layer 14. The port 18 is secured to the muscle tissue 16 by means of sutures (not shown). The fluid receptacle 18 includes walls 20 which define a fluid reservoir 22. The walls 20 join at a relatively flat upper surface 24 opposing the skin layer 10. A physician, or others who are trained and skilled in fluid injection, locate the upper surface 24 by means of palpitation on the patient's skin 10. The catheter access port includes a catheter 26 which extends from the reservoir 22 to a site (not shown) to which the therapeutic fluid is intended to be delivered. The upper surface 24 of the catheter access port is formed of a self-sealing membrane which is puncturable by a needle but reseals upon withdrawal of the needle. It will be appreciated, that a catheter access port as described is well known in the art and forms no part of this invention per se.

To inject fluid into the reservoir 22, a physician locates the upper membrane area 24 and determines a point 30 of puncture. A needle 32 is inserted through the skin 10 with the needle tip 34 puncturing the skin at point 30 and passing through the membrane 24 into the reservoir 22. The membrane 24 maintains a seal around the needle at the point of puncture of the membrane 24. An inlet end 36 of needle 32 is connected to an appropriate supply of therapeutic fluid via tubing 38. As shown, needle 32 is a Huber-type needle which has a 90 degree bend 40 between a first segment 42 extending between the bend 40 and insertion tip 34 and a second portion 44 extending between bend 40 and inlet end 36. Although it will be apparent that the present invention will be suited for needles other than the Huber-type needle, the Huber needle is shown in the preferred embodiment since the Huber needle is currently approved for use with receptacles such as access port 18 since the configuration of the needle tip 34 minimizes damage to the self-sealing membrane 24.

The needle 32 is maintained with tip 34 received within reservoir 22 for a time sufficient to administer fluid from a source (not shown) to fill the reservoir 22. Depending upon the circumstances and the type of fluid receptacle 18 being filled, the time of insertion may last from a few minutes to more than several hours. To support the needle 32 with tip 34 within reservoir 22 during this period of injection, a needle support 50 of the present invention is supplied.

Figure 2:
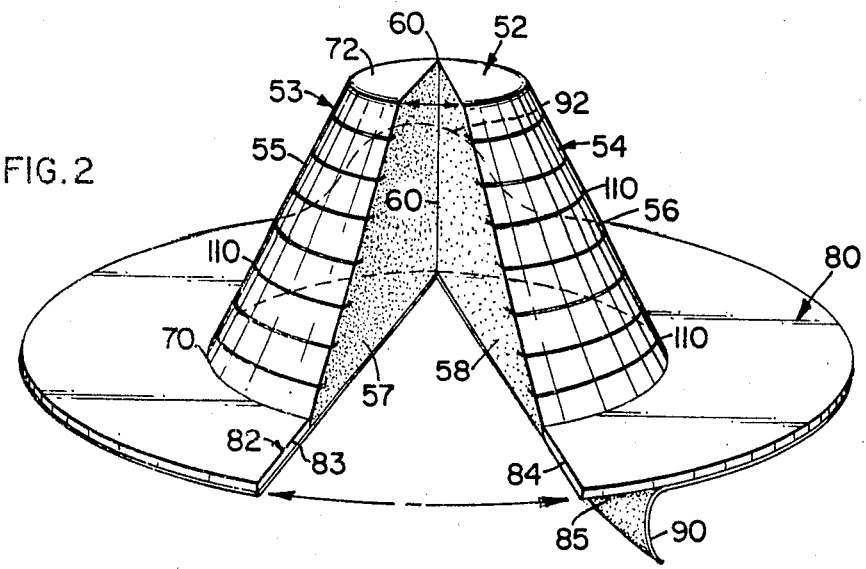
FIG. 2 is a perspective view of a needle support according to the present invention.

The needle support 50 includes a frusto-conical body 52 which is split along a plane which includes its conical axis to separate the body 52 into a first semiconical half 53 and a second semiconical half 54. Each of the conical halves 53 and 54 have a semiconical surface 55 and 56, respectively, and a flat planar surface 57 and 58 which are coincident with the conical axes of the halves 53 and 54. As best shown in FIG. 2, the conical halves 53 and 54 are joined on a hinged edge 60 which joins the edges defined by surfaces 55 and 57 and surfaces 56 and 58, respectively. So joined, the semiconical halves 53 and 54 are pivotable about hinge 60 with flat planar surfaces 57 and 58 opposing one another and pivotal between an open position as shown in FIG. 2 and a closed position as shown in FIG. 1. The semiconical halves 53 and 54 are formed of a material which, for reasons which will be described, are rigid yet deformable about a metal injection needle such as needle 32. A suitable preferred material would be polypropylene.

Body portions 53 and 54 may be hinged at hinge edge 60 by applying a tape joining the halves 53 and 54. Preferably, the portions 53 and 54 are hinged by slicing partially through a solid polypropylene body and leaving sufficient material at hinge edge 60 for the halves 53 and 54 to be separated a spacing sufficient to place the semiconical halves 53 and 54 around needle 32. When the halves 53 and 54 are pivoted to a closed position, the opposing flat surfaces 57 and 58 abut one another over their entire surface area.

As shown in the drawings, the body portion 52 includes a large diameter radial base 70 and an axially displaced small diameter radial base 72. A ring support 80 is provided secured to base 70 and extends radially away from base 70. The support 80 is formed of flexible material which may be bonded to base 70 in any suitable manner such as by heat bonding but is preferably made integral with the body 52 and formed of polypropylene of sufficient thinness to be flexible. The ring support 80 is provided with a radial cut 82 to provide opposing surfaces 83 and 84 of the support 80 which are aligned with surfaces 57 and 58. A surface of the support 80 on a side thereof opposite body 52 is provided with a bacteriocidal adhesive coating 85. A removable backing sheet 90 of plastic or the like is preferably maintained in contact with the coating 85 of support 80 to prevent the coating from becoming attached to material other than the patient's skin prior to placement of the device around a needle 32 as will be described.

As shown, ring support 80 is a flat ring surrounding support body 52. To further secure needle support 50, adhesive bandages can be disposed on top of support 80 and extending onto the patient's skin 10.

In use of the needle support 50, a health care provider who has injected needle tip 34 into reservoir 22, removes backing sheet 90 and separates first semiconical half 53 from second semiconical half 54 by pivoting the two halves about hinge edge 60. The flexible nature of support 80 generates a bulge 92 which accommodates the opening of the body portion 52 as shown in FIG. 2. With the body portion 52 opened as shown in FIG. 2, the body portion is inserted with the needle portion 42 disposed between the opposing surfaces 57 and 58. With the needle portion 42 so disposed, the body halves 53 and 54 are pivoted to the closed position (as shown in FIG. 1) and the support 80 is adhered to the skin 10 by coating 85.

As the body halves are pivoted about hinge 60 to the closed position, the surfaces 57 and 58 become coplanar and the material of the surfaces which abut the needle portion 42 deform around the rigid needle to define a needle receiving channel 100 with the needle portion 42 snugly secured within channel 100 between the abutting surfaces 57 and 58. The body halves 53 and 54 are maintained in the closed position through any suitable means such as by applying a tape around the outer surfaces 55 and 56 or by providing one of the surfaces (for example surface 57) with snap pins and providing the opposing surface with snap pin receiving holes. However, a preferred embodiment would be to provide both surfaces 57 and 58 with an adhesive and a removable backing sheet which is removed prior to pivoting the body portions to the closed position around needle 42 with the adhesives joining surfaces 57 and 58 together surrounding needle portion 42.

From the foregoing, it can be seen that the needle portion 42 is captured within channel 100 defined by deformed portions of surfaces 57 and 58. The precise orientation of the needle portion 42 is not important since the channel 100 will be formed wherever the surfaces 57 and 58 happen to engage the needle 42. The needle portion 42 may be off center from the body 52 or at an angle with respect to the conical axis of the body 52 and still be securely held by body 52. Therefore, the needle support 50 is adapted for quick and easy installation in that a health care provider can, after inserting the needle 32 into the reservoir 22, readily and quickly insert the support 50 without having to accurately align any needle receiving portion of the support 50 with needle portion 42. The deformable nature of the rigid body defines the needle receiving channel 100 to be wherever the needle portion 42 happens to abut the surfaces 57 and 58.

While the above described needle support 50 is adaptable for use with any type of needle, is it intended that due to the present acceptance of a Huber needle with implantable receptacles, the primary use would be with a Huber needle such as needle 32. A needle support must have a length less than a distance between needle portion 44 and a patient's skin 10. Huber needles currently available are provided with a needle portion 42 having a length from tip 34 to bend 40 of three quarter inch, one inch, one and one quarter inch, one and one half inch, two inch, and two and one half inches. While a variety of needle supports 50 having varying axial lengths could be provided, it is preferred that the needle support 50 could be made in one size which would be modified by the health care provider to accept a Huber needle of given dimension. To this end, the body portion 52 is provided with a plurality of circumferential slits 110 axially spaced every quarter inch from support 80. Accordingly, a health care provider can use the slits 110 as a guide in placing a knife or other suitable tool to trim the axial length of the body member 52 to accept a Huber needle of given size.

From the foregoing, it can be seen how the objects of the present invention have been attained in a preferred manner. However, it is not intended that the scope of this invention be limited by the specific embodiment described and that the invention will include such modifications and equivalents as will occur to those skilled in the art. Therefore, it is intended that the scope of the invention will be limited only by the scope of the claims as are appended hereto.

What is claimed is:

1. A support for a rigid tubular needle to be inserted into a body part of a patient and retained therein for a period of time; comprising:
    a rigid body portion having opposing members presenting opposing needle engaging surfaces, said opposing needle engaging surfaces contoured to lie in face-to-face contact in an intended neeedle retaining area when said surfaces are disposed abutting one another with an absence of said needle between said surfaces, said surfaces sized to oppose a needle disposed within said needle retaining area when said needle is oriented in any of a plurality of positions with said needle generally parallel to said surfaces, said members formed of a material selected to have rigidity for said surfaces to support said needle and deform around said needle when said needle engaging surfaces are disposed abutting one another with said needle present between said surfaces and with deformation of said surfaces around said needle avoiding a collapse of said needle;
    means for connecting said opposing members with said needle engaging surfaces urged together to deform around a rigid needle disposed between said surfaces;
    securing means for securing said body portion to a patient's skin; and
    said rigid body portion being sized to extend away from said securing means on a side of said securing means opposite an intended patient contacting side.

2. A support for a rigid tubular needle to be inserted into a body part of a patient and retained therein for a period of time, comprising:
    a rigid body portion having a first member and a second member having flat surfaces, said flat surfaces of said first and second members contoured to lie in face-to-face contact in an intended needle retaining area when said flat surfaces are disposed opposing and abutting one another with an absence of said needle between said surfaces, said surfaces sized to oppose a needle disposed with said needle retained area when said needle is oriented in any of a plurality of positions and with said needle generally parallel to said surfaces;
    hinge means for pivotally connecting said members to pivot about a hinge axis between an open position with said flat surfaces opposing and spaced apart to define a needle receiving opening, and a closed position with said flat surfaces opposing and abutting one another in said face-to-face contact;
    a support member secured to said body portion and disposed to engage a patient's skin, said rigid body portion being sized to extend away from said support member on a side thereof opposite an intended patient contacting side, said surfaces generally normal to a patient's skin when said patient contacting side is disposed against said patient's skin;
    an adhesive secured to said support member to adhere said support member to a patient's skin;
    a backing member sized to cover said adhesive; and
    said body portion members formed of a material selected to have rigidity to support a needle extending from a patient's body between said flat opposing abutting surfaces and for said surfaces to deform around said needle with opposing deformed surfaces defining a needle support channel when said surfaces are disposed abutting one another with said needle present between said surfaces and with deformation of said surfaces around said needle avoiding a collapse of said needle.

3. A support for a needle according to claim 2 including means for fastening said body portion members together with said flat opposing surfaces abutting one another with a needle disposed between deformed portions of said surfaces.

4. A support according to claim 3 wherein said body is scored at a plurality of axially displaced positions to provide indicia to trim said body portion to a length sized to receive a needle of predetermined length.

5. A needle support for securely holding and protecting a rigid tubular injection needle when said needle is inserted into a body part of a patient; said device comprising:
    a rigid body portion comprising a first base portion and a second base portion with hinge means for pivotally securing said first asnd second portions about a common hinge axis;
    said base portions having opposing planar surfaces which are contoured to lie in face-to-face contact in an intended needle retaining area when said portions are pivoted about said axis to a closed position and with an absence of said needle between said surfaces in said closed position, said surfaces sized to oppose a needle disposed within said needle retaining area when said needle is oriented in any of a plurality of positions with said needle generally parallel to said surfaces;

said surfaces formed of a rigid material selected to be deformable about a rigid injection needle when said needle disposed between said opposing planar surfaces in said closed position and with deformation of said surfaces around said needle avoiding a collapse of said needle;

means for securing said portions in said closed position;

a base member secured to said rigid body portion aligned to rest on a patient's skin;

adhesive means for adhering said base member to a patient's skin; and said rigid body portion being sized to extend away from said base member on a side thereof opposite said adhesive means.

6. A device according to claim 5 wherein said base portions are provided with markings disposed a predetermined distance from said base member representing predetermined lengths of needles to be supported by said device.

* * * * *